(12) United States Patent
Sharpe et al.

(10) Patent No.: US 9,442,059 B2
(45) Date of Patent: *Sep. 13, 2016

(54) UV DIODE LASER EXCITATION IN FLOW CYTOMETRY

(75) Inventors: Johnathan Charles Sharpe, Hamilton (NZ); Donald Francis Perrault, Boston, MA (US)

(73) Assignee: XY, LLC, Navasota, TX (US)

( * ) Notice: Subject to any disclaimer, the term of this patent is extended or adjusted under 35 U.S.C. 154(b) by 129 days.

This patent is subject to a terminal disclaimer.

(21) Appl. No.: 14/114,150

(22) PCT Filed: May 11, 2012

(86) PCT No.: PCT/US2012/037645
§ 371 (c)(1),
(2), (4) Date: Nov. 13, 2013

(87) PCT Pub. No.: WO2012/155106
PCT Pub. Date: Nov. 15, 2012

(65) Prior Publication Data
US 2014/0092378 A1    Apr. 3, 2014

Related U.S. Application Data

(60) Provisional application No. 61/485,566, filed on May 12, 2011.

(51) Int. Cl.
| | | |
|---|---|---|
| *G01N 15/14* | (2006.01) | |
| *G01N 21/64* | (2006.01) | |
| *G01N 21/55* | (2014.01) | |
| *G01N 21/49* | (2006.01) | |

(52) U.S. Cl.
CPC .............. *G01N 15/14* (2013.01); *G01N 21/49* (2013.01); *G01N 21/55* (2013.01); *G01N 21/64* (2013.01); *G01N 21/6486* (2013.01); *G01N 2015/149* (2013.01)

(58) Field of Classification Search
None
See application file for complete search history.

(56) References Cited

U.S. PATENT DOCUMENTS

| | | |
|---|---|---|
| 4,327,972 A | 5/1982 | Brunsting |
| 5,895,922 A | 4/1999 | Ho |
| 6,149,867 A | 11/2000 | Seidel et al. |
| 6,263,745 B1 | 7/2001 | Buchanan et al. |
| 6,335,790 B1 | 1/2002 | Andresen et al. |
| 6,357,307 B2 | 3/2002 | Buchanan et al. |
| 6,366,354 B1 | 4/2002 | Chandler |

(Continued)

FOREIGN PATENT DOCUMENTS

| | | |
|---|---|---|
| WO | 9918595 A1 | 4/1999 |
| WO | 2010148332 A2 | 12/2010 |

OTHER PUBLICATIONS

Telford, William G., "Chapter 23. Small Lasers in Flow Cytometry"; Chapter; pp. 399-418; Methods in Molecular Biology: Flow Cytometry Protocols, 2nd ed (20 pages).

(Continued)

*Primary Examiner* — Gordon J Stock, Jr.
(74) *Attorney, Agent, or Firm* — Ryan Christensen; Hashim Rahman

(57) ABSTRACT

The present invention generally relates to a method and apparatus for exciting particles, and more specifically relates to analyzers or sorters for exciting fluorescently labeled particles with a multimode diode laser and the optics for making high resolution determinations from the multimode diode laser beam excitation.

28 Claims, 6 Drawing Sheets

(56) References Cited

U.S. PATENT DOCUMENTS

| | | | |
|---|---|---|---|
| 6,782,768 | B2 | 8/2004 | Buchanan et al. |
| 7,397,546 | B2 | 7/2008 | Weber et al. |
| 8,502,976 | B2 | 8/2013 | Sharpe et al. |
| 2003/0098421 | A1 | 5/2003 | Ho |
| 2004/0042008 | A1* | 3/2004 | Wagner .................. G01N 15/14 356/337 |
| 2006/0113289 | A1 | 6/2006 | Ehrmann et al. |
| 2006/0256335 | A1* | 11/2006 | Chen ..................... G02B 5/3083 356/369 |
| 2007/0117086 | A1 | 5/2007 | Evans et al. |
| 2009/0059202 | A1 | 3/2009 | Ueno |
| 2010/0059490 | A1* | 3/2010 | Unrath ............... B23K 26/0613 219/121.73 |
| 2010/0208356 | A1 | 8/2010 | Cayer |
| 2010/0290041 | A1 | 11/2010 | Graham |
| 2010/0314557 | A1 | 12/2010 | Hayashi et al. |
| 2011/0176127 | A1* | 7/2011 | Kanda ................ G01N 15/1429 356/72 |

OTHER PUBLICATIONS

Telford, William, et al.; "Violet Laser Diodes in Flow Cytometry: An Update"; Article, 2006, pp. 1153-1160, vol. Part A 69A; Cytometry (8 pages).

Sharpe, J. C., et al.; "Advances in flow Cytometry for Sperm Sexing"; Article, 2009, pp. 4-10; vol. 71, Theriogenology (7 pages).

Holc, Katarzyna Anna, "Integrated Optical Systems Based on GaN Laser Diodes and Some Application to Spectroscopy"; Ph.D. Dissertation, Oct. 2010, Institute of High Pressure Physics, Polish Academy of Sciences (132 pages).

PCT International Search Report and Written Opinion dated Oct. 9, 2012, issued in corresponding PCT Application No. PCT/US2012/037645 (12 pages).

US Office Action dated Jan. 17, 2013, issued in corresponding U.S. Appl. No. 13/470,173 (10 pages).

US Notice of Allowance dated May 31, 2013 issued in corresponding U.S. Appl. No. 13/470,173 (8 pages).

Singapore Search and Examination Report dated May 13, 2014, issued in related SG Application No. 2013080411 (15 pp).

Johnson. L. A., et al. "Modification of a laser based flow cytometer for high resolution DNA analysis of mammalian spermatozoa" Cytometry 7.3 (1986): 268-273.

Johnson Lawrence A., "Sex preselection by flow cytometric separation of X and Y chromosome-bearing sperm, based on DNA difference: a review." Reproduction, Fertility and Development 7.4 (1995): 893-903.

Shapiro, Howard M., "Beam Profiles and Beam Quality", Practical Flow Cytometry. 4th Ed. John Wiley & Sons, 2003, (pp. 136-138).

Extended European Search Report for EPO Appl. No. 12782271.6 issued on Feb. 3, 2015.

Chinese Office Action dated May 15, 2015 issued in related CN Appl. No. 201280022789.X.

Chinese Office Action dated Jan. 4, 2016 issued in related CN Application No. 201280022789.X.

\* cited by examiner

Laser Output Beam Profile – Flow Axis

Laser Output Beam Profile – Transverse Flow Axis 2D contour Plot Beam Profile

Beam Shaping Optics Beam Profile – Flow Axis

Beam Shaping Optics Beam Profile – Transverse Flow Axis

2D Contour Beam Profile

UV DIODE LASER EXCITATION IN FLOW CYTOMETRY

CROSS-REFERENCE TO RELATED APPLICATIONS

This Application is a National Stage entry of Patent Cooperation Treaty International Application No. PCT/US2012/037645, filed May 11, 2012, which claims priority to U.S. provisional Application No. 61/485,566, filed May 12, 2011, the entire contents of both are incorporated herein by reference.

FIELD

The present invention generally relates to a method and apparatus for exciting particles, and more specifically relates to analyzers or sorters for exciting fluorescently labeled particles with a multimode diode laser and the optics for making high resolution determinations from the multimode diode laser beam excitation.

BACKGROUND

There exists a motivation to decrease the overall cost and size of flow cytometry equipment, particularly in laboratory and industrial applications, such as in sperm sorting. Currently, sperm sorting and other flow cytometry applications operating at ultraviolet wavelengths require expensive, bulky, energy high consumption excitation sources. In sperm sorting and other UV applications a significant demand is placed on the laser for obtaining sufficient laser power, at an appropriate wavelength for optimum excitation, with a uniform spatial beam profile, and with sufficiently low noise to provide the necessary fidelity required to resolve minor differences between various particles. Recent developments in solid state and diode lasers have held much promise for replacing commercial lasers with smaller, more efficient, lower cost lasers, however the combined power, wavelength, spatial uniformity, and cost requirements have not yet been met by these systems.

Nichia (a Japanese Corporation) released the first commercially available 'high power' (i.e. >20 mW) UV laser diode as engineering samples. However, the specifications of this system, at glance, appear unsuitable for certain applications, such as sperm sorting. The 370 to 380 nm, 200 mW system does not appear capable of meeting the power and profile requirements for making high resolution DNA content measurements. Such lasers appear unsuitable for sorting sperm because of the presence of multiple simultaneous lasing modes that result in a highly irregular, or variable, spatial intensity pattern across the laser beam profile (perpendicular to the axis of propagation). These unfavorable attributes are expected to make the released UV diode laser unsuitable for application to sperm DNA content measurements. Further, while the 200 mW power output specified may suggest that such an excitation source might be a drop-in replacement for a 150 mW pulsed 80 MHz NdYAG laser operating at 355 nm, the excitation efficiency of the primary fluorescent dye (Hoechst 33342) used for sperm sorting drops from near 100% (at 355 nm) to approximately only 50% over the 370 to 380 nm range. Thus, in order to match the energy delivered by the NdYAG laser to achieve similar excitation power and fluorescence response (to obtain a good X-Y 'split'), one would require a 50% increase in the 200 mW provided in this unit. Further restricting the potential for using such a system, once assembled into an integrated laser module, it is difficult to maintain a full 200 mW with coupling losses, and if laser diode lifetime is a concern, it is recommended that lasers be operated at input currents that produce even lower powers to avoid premature component failure.

DISCLOSURE OF INVENTION

Embodiments described herein generally relate to systems and methods for incorporating a multimode diode laser into analyzers and sorters.

In some embodiments, an instrument with beam shaping optics produces a suitable analyzer or sorting device utilizing a multimode diode laser, such as a multimode diode laser operating at an ultraviolet wavelength and having a beam profile with variable spatial intensity characteristics. An object of some embodiments may be to create a flow cytometer system incorporating a smaller, lighter multimode UV diode laser capable of illuminating fluorescent dyes, such as Hoechst 33342, with high resolution; for example, with enough resolution to distinguish X-chromosome bearing sperm from Y-chromosome bearing sperm which, depending upon the species, generally vary by 2-5%.

In some embodiments, an instrument may include flow cytometer components for delivering particles along a flow axis to an interrogation zone and a multimode diode laser for producing a multimode beam along a beam axis that illuminates particles at the interrogation zone. The multimode beam may have a beam profile with variable spatial intensity characteristics and that beam profile may be modified with beam shaping optics in the beam axis. The modified beam profile may have uniform spatial intensity characteristics. Reflected and/or fluoresced light from the illuminated particles may be picked up by a detector which produces signals representative of particle characteristics and a processor can analyze that signal for determining particle characteristics and producing sort decisions.

Some embodiments relate to a method of processing particles, such as analyzing or sorting particles, utilizing a multimode diode laser which may have a beam profile with variable spatial intensity characteristics. Such a method may begin by flowing particles along a fluid flow path having an interrogation zone. A multimode beam having variable spatial intensity characteristics may be directed at the interrogation zone and manipulated with beam shaping optics to form a beam with uniform spatial intensity characteristics. Particles at the inspection zone may then be illuminated with the manipulated beam and light which is reflected or fluoresced from the particles may be detected for classifying particles.

A further object of the present invention may be to manipulate a spatially variable beam with a second spatially variable beam to produce a beam with more uniform, or near-uniform, spatial intensity characteristics.

Naturally further objects of the invention are disclosed throughout other areas of the specification and claims.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODES FOR CARRYING OUT THE INVENTION

Figure 1:
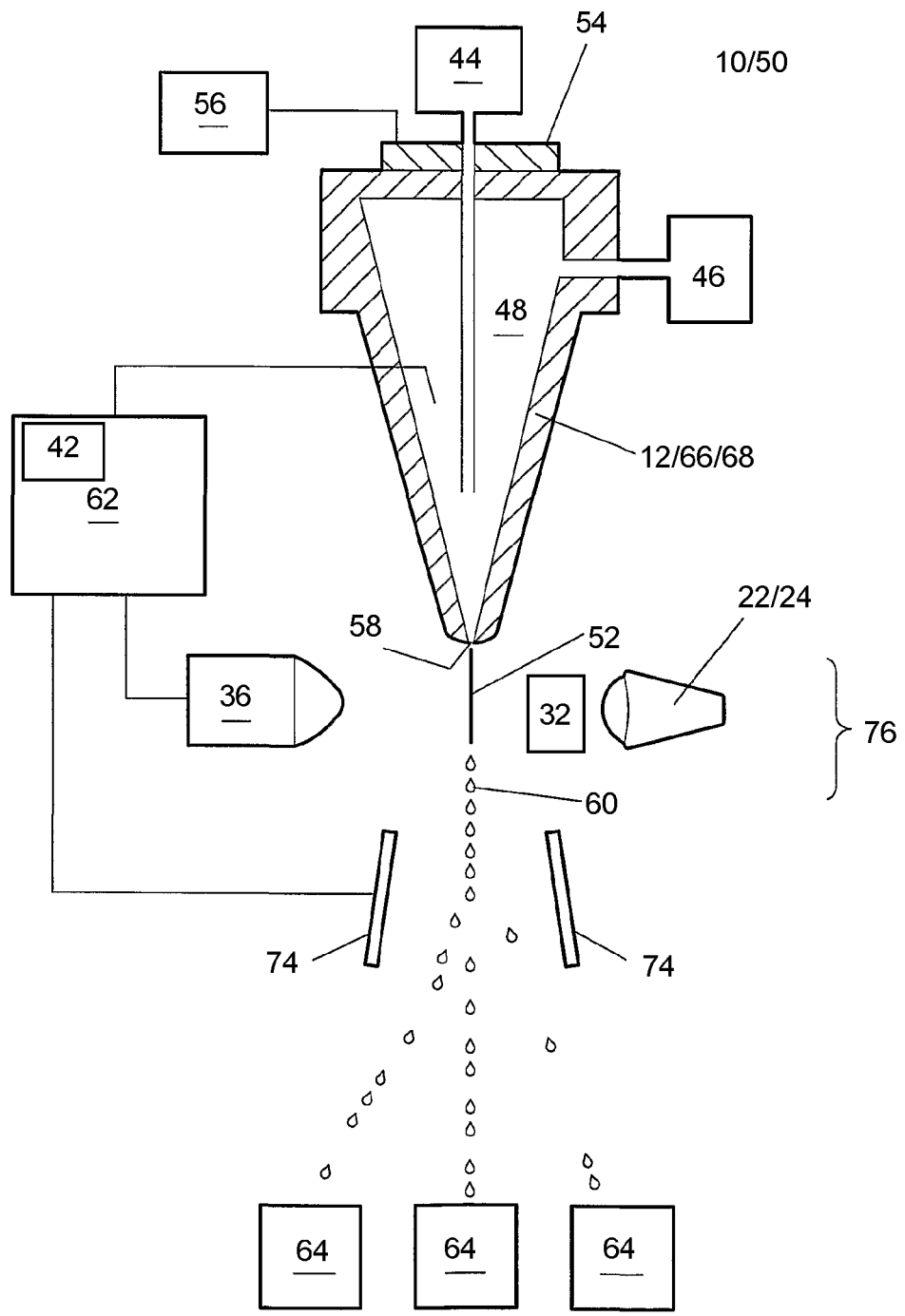
FIG. 1 illustrates a schematic of a flow cytometer including a multimode diode laser and beam shaping optics.
Figure 2:
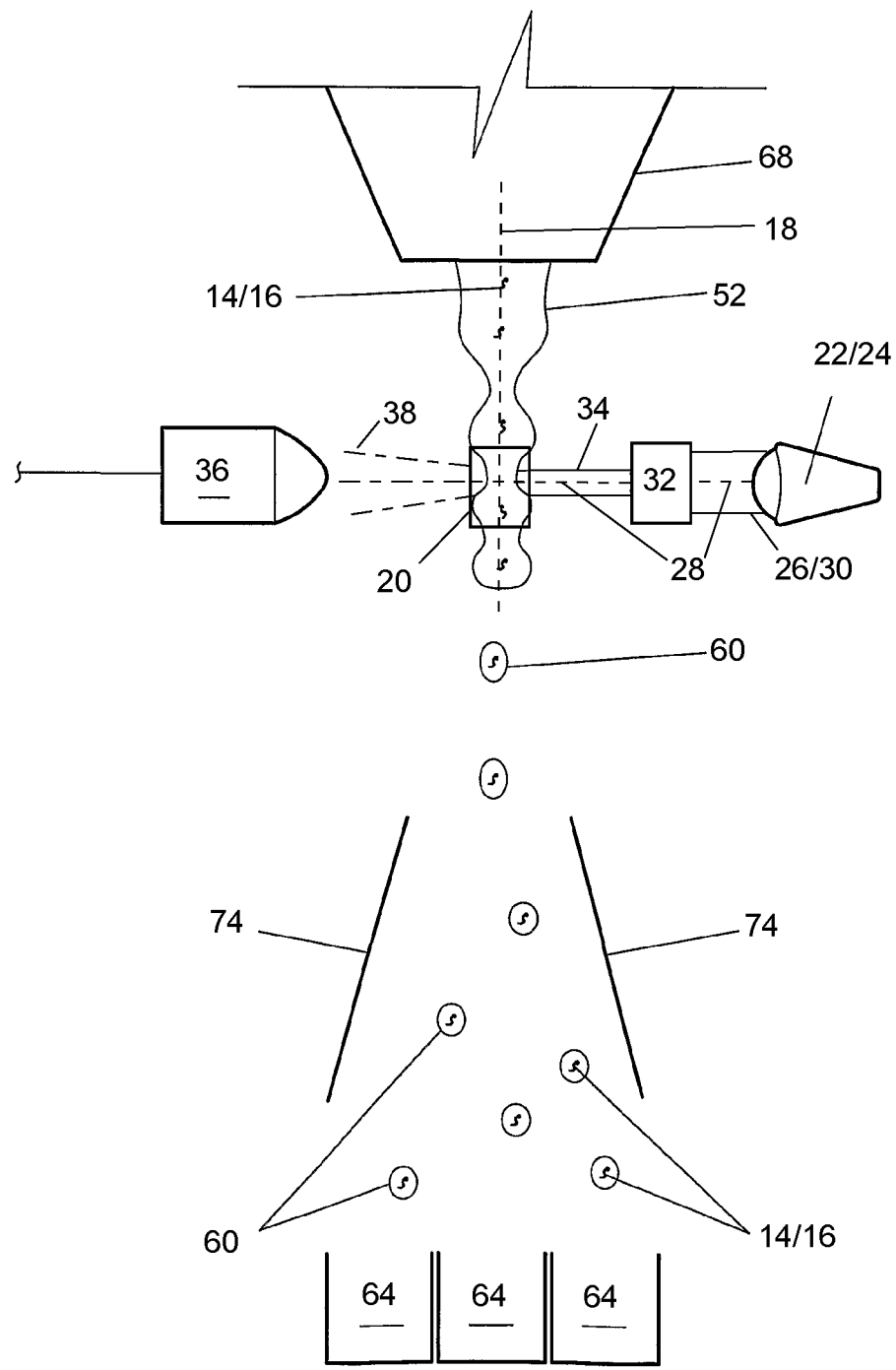
FIG. 2 illustrates a closer view of some features of the flow cytometer illustrated in FIG. 1.

Referring primarily to FIG. 1 and FIG. 2, an instrument (10) is illustrated as a flow cytometer (50) for sorting particles (14), such as sperm cells (16). It should be understood; other particles and cells may also be analyzed and/or sorted with similar instruments. Sperm cells (16) serve as an example of particles requiring high resolution fluorescent measurements to differentiate particular cell characteristics. While FIG. 1, and other figures and portions of the description reflect a jet-in-air flow cytometer (50), other sorters and analyzers may benefit from the present invention. Such instruments may include, without limitation, epi-illumination analyzers and sorters, laser ablation sorters (zappers), closed chamber analyzers and sorters, and microfluidic chip analyzers and sorters.

The particles (14) or cells, such as sperm cells (16) may be deposited within a flow source (12), such as a nozzle (68) in a manner allowing the particles (14) to be surrounded by sheath fluid (48) and introduced into a fluid stream (52) through a nozzle orifice (58). The nozzle (68) may be provided with a suitable internal geometry to serve as an orienting device (66) for biasing the particles (14) in the fluid stream (52) in a desired orientation. U.S. Pat. Nos. 6,263,745; 6,782,768; and 6,357,307 provide non-limiting examples of suitable internal geometries for an orienting device and are incorporated herein by reference in their entirety. The sheath fluid (48) may be supplied by a sheath fluid source (46) so that as the flow source (12) supplies the particles (14) into the sheath fluid (48) concurrently as they are fed through the nozzle (68). In this manner, the sheath fluid (48) may form a sheath fluid environment for the particles.

An oscillator (54), such as a piezoelectric crystal, may be precisely controlled through an oscillator control (56), to establish pressure waves within the nozzle (68) and to the fluids exiting nozzle orifice (58). The pressure waves generated by the oscillator (54) acts upon the sheath fluid (46), the stream (52) exiting the nozzle orifice (58) to regularly forms drops (60) some distance downstream of the nozzle orifice (58). The particles (14) surrounded by the fluid stream (52) become entrained within individual drops (60) and may be isolated for collecting particles with specific measured characteristics.

The measured characteristics may be determined through a particle or cell sensing system (76). The particle or cell sensing system (76) may include a detector (36) which responds to the particles (14) contained within fluid stream (52). The particle or cell sensing system (76) may generate a signal representative of the relative presence or relative absence of a characteristic. The particle or cell sensing system (76) may also generate a signal representative of a quantitative value, such as an amount of fluorochrome bound to DNA within a cell which has been excited by an irradiation source such as a laser (22).

Figure 4A:
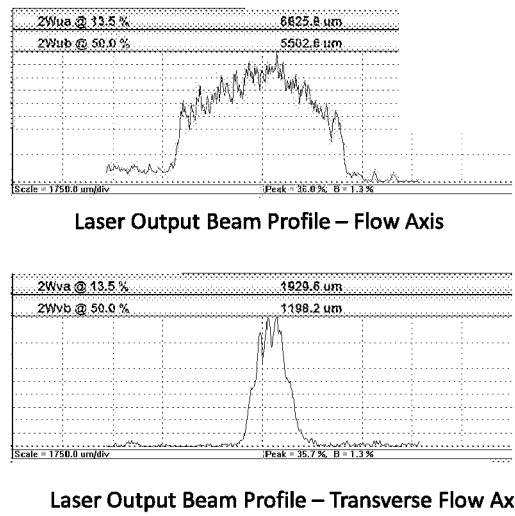
FIG. 4A-B illustrates beam profiles for manipulated and unmanipulated multimode diode lasers.
Figure 4A:
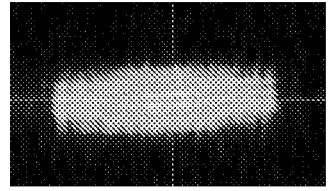
Figure 4B:
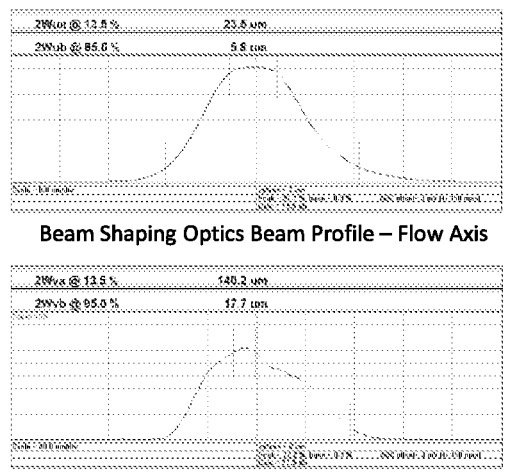
Figure 4B:
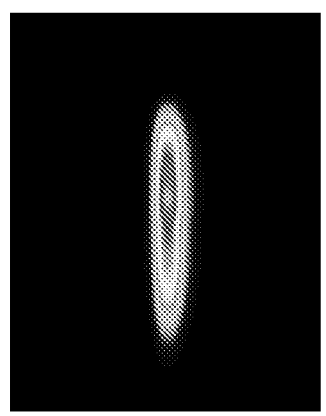
Figure 5:
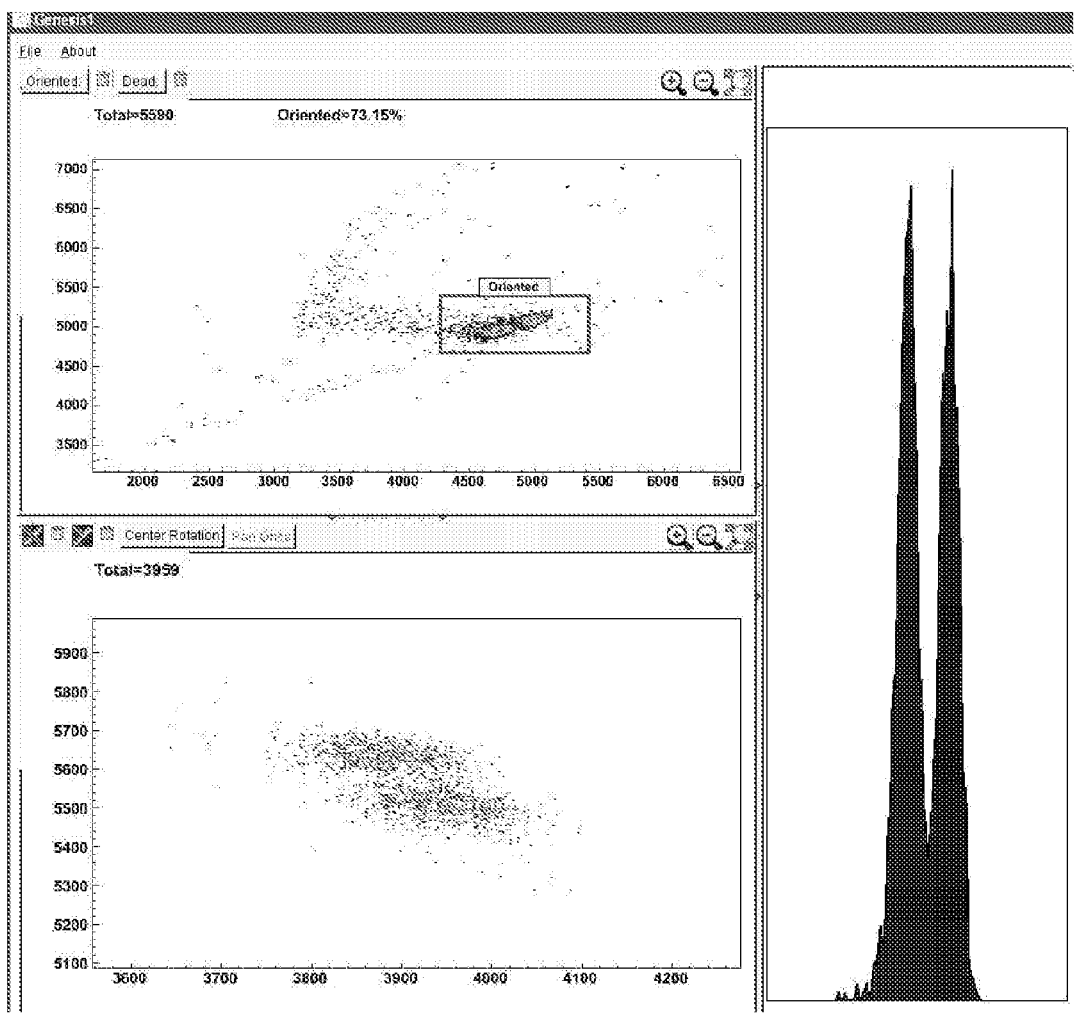
FIG. 5 illustrates a histogram and bivariate plot of a sperm sorting application of a multimode laser and beam shaping optics.

The laser (22) used for such an excitation may be a multimode diode laser (24). As one example, the multimode diode laser (24) can operate at an ultraviolet wavelength, such as between about 350 nm and about 400 nm, or between about 370 nm and about 380 nm. Referring briefly to FIG. 4A a beam profile can be seen for one such multimode diode laser (24) operating in the ultraviolet frequency range. Across the longest axis spatial variations in the beam intensity can be seen as a series of peaks. This profile may be considered to have variable spatial intensity characteristics, as the beam intensity is variable moving away from the beam center point. In analyzer and sorting applications a Gaussian beam profile may be desirable because as particles traverse slightly different paths across the beam spot they may receive slightly different total exposure. A Gaussian profile, while not perfect, provides for more uniform exposure to particles that traverse slightly different paths across the beam spot. In contrast, the profile depicted in 4B presents a great deal of abrupt intensity variations. For these reasons, the irregular shape of the multimode diode laser (24) is very undesirable for sorting and analyzing operations. It has surprisingly been found that the beam produced by such multimode diode laser (24) can pass through beam shaping optics (32) before illuminating, or exciting, particles (14) within the stream (52), and can be compressed to a near uniform or pseudo-Gaussian beam profile. Surprisingly, this configuration can provide a beam profile suitable for applications such as sorting sperm (which requires differentiating very small difference in DNA content), as seen in FIG. 5. The manipulated beam profile is seen in FIG. 4B demonstrates uniform spatial intensity characteristics. As used herein the term "uniform," as well as pseudo-Gaussian, should be understood to include beam profiles that present a relatively smooth intensity profiles, or profiles with relatively consistent changes moving away from a beam center, as opposed to the spatial variations in intensity illustrated as multiple nodes.

Referring to FIG. 2, the multimode diode laser (24) illustrated produces a multimode beam (26) along a beam axis (28). The multimode beam (26) produced at the multimode laser (24) has a beam profile with variable spatial intensity characteristics (30). The beam shaping optics (32) located on the beam axis (28) receive the multimode beam 26 and produces a manipulated beam profile with uniform spatial intensity characteristics (34). Once the manipulated beam reaches an interrogation zone (20), particles (14), or sperm (16), along a flow axis (18) of fluid stream (52) are illuminated exciting autofluorescence as well as fluorochrome dyes and produce reflected and/or fluoresced light (38). This reflected or fluoresced light (38) can be picked up and measured by a detector (36).

Particles, cells, or nuclear DNA may be stained with at least one type of fluorochrome and different amounts of fluorochrome may bind to each individual particles or cells based on the number of binding sites available to the particular type of fluorochrome used. With respect to spermatozoa, the availability of binding sites for Hoechst 33342 stain depends on the amount of DNA contained within each sperm cell. Because X-chromosome bearing spermatozoa contain more DNA than Y-chromosome bearing spermatozoa, the X-chromosome bearing spermatozoa can bind a greater amount of fluorochrome than Y-chromosome bearing spermatozoa. Thus, by measuring the fluorescence emitted by the bound fluorochrome upon excitation, it is possible to differentiate between X-bearing spermatozoa and Y-bearing spermatozoa.

Referring back to FIG. 1, means to achieve separation and isolation based upon particle or cell characteristics are depicted. The reflected or fluoresced light (38) can be received by detector (36) and fed to a separation discrimination system or analyzer (62) having a processor (42) for classifying particles (14) and/or making sort decisions. The separation discrimination system or analyzer (62) may be coupled to a droplet charger which differentially charges each droplet (60) based upon the characteristics of the particle or cell contained within that droplet (60). In this manner the separation discrimination system or analyzer (62) acts to permit the electrostatic deflection plates (74) to deflect drops (60) based on whether or not they contain the appropriate particle or cell. Other separation techniques and devices, such laser ablation or fluid switching, may be used in place of the droplet charger and deflection plates (74).

As a result, the flow cytometer (50) acts to separate the particle or cells by causing them to be directed to one or more collection containers (64). For example, when the analyzer differentiates sperm cells based upon a sperm cell characteristic, the droplets entraining X-chromosome bearing spermatozoa can be charged positively and deflected in one direction, while the droplets entraining Y-chromosome bearing spermatozoa can be charged negatively and deflected the other direction. A waste stream may include droplets that do not entrain a particle or cell or entrain undesired or unsortable cells and can be left uncharged to collect in an undeflected stream into a suction tube, or the like. One such system is discussed in U.S. Pat. No. 6,149,867, hereby incorporated by reference herein. Naturally, numerous deflection trajectories can be established with various degrees of positive and/or negative charges for producing multiple streams in each direction which can be collected simultaneously.

Figure 3:
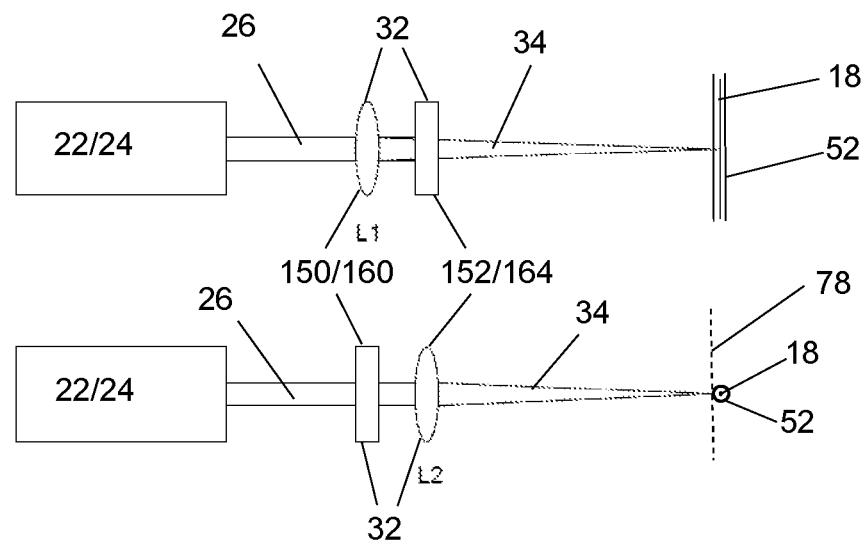
FIG. 3 illustrates two views of a schematic for beam shaping optics and a multimode diode laser.

FIG. 3 provides an illustration of one example of beam shaping optics (32) used to bring the multimode diode laser (24) into a beam profile suitable for analyzing cells in a flow cytometer (50). L1 is illustrated as a first element (150), or first cylindrical lens (160), and L2 is illustrated as a second element (152), or second cylindrical lens (164) to focus and shape the spatially uneven multimode laser profile. FIG. 3 illustrates L1 and L2 as cylindrical lenses that are crossed, or oriented at 90° relative to each other, but it should be appreciated either one of L1 or L2 could be replaced with a spherical lens. Other optical elements for performing similar or equivalent functions may also be used. In the embodiment illustrated, L1 transforms the multimode beam in the flow axis (18), while L2 acts to compress the multimode beam (26) along the beam width, or in the transverse flow axis (78). Surprisingly, it was found with sufficient compression in the transverse flow axis (78), a multimode diode laser (24) could be compressed to a suitable beam shape for sorting sperm and would have a uniform enough intensity profile for differentiating small variations in DNA content. This configuration was able to transform the multi-node, non-Gaussian beam profile, illustrated in FIG. 4A, to the profile having a more uniform intensity distribution, seen in FIG. 4B. The adjusted beam profile need not necessarily be Gaussian, or even near-Gaussian, but should provide each particle that passes through a very constant dosage of laser power, even when there are slight variations in the path each particle traverses through the beam spot. Surprisingly, this configuration was able to achieve an X-Y split suitable for sex sorting sperm as illustrated in a fluorescence histogram and bivariate plot in FIG. 5. Non-limiting examples of beam profiles which may be used include: Gaussian, flat top, rectangular, trapezoidal and combinations thereof.

As one non-limiting example, L1 may have a focal length of 80 mm and L2 may have a focal length of 30 mm. In the described configuration these lenses may be used to produce a beam profile having a shape having a width or roughly 140 μm and a height of roughly 24 μm. Other similar configurations are contemplated herein which may include highly compressing a beam width of a multimode mode laser, and shaping the beam to a suitable beam spot for sorting sperm.

Figure 6:
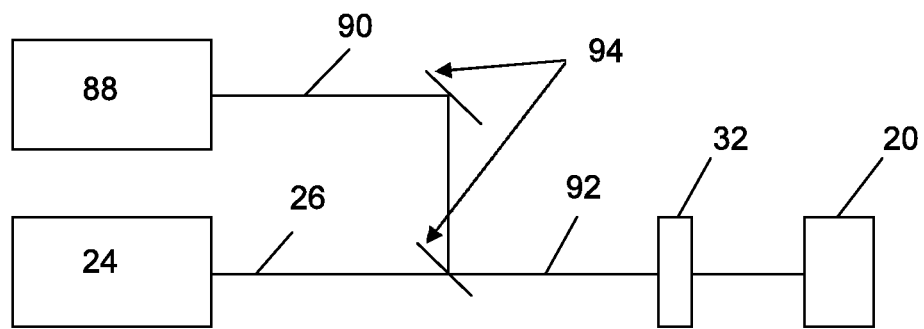
FIG. 6 illustrates an embodiment combining two multimode laser beams.

Turning now to FIG. 6, an alternative embodiment is depicted where the multimode diode laser (24) is combined with a second multimode diode laser (88). Optics (94) are illustrated for combining the multimode beam (26) with a second multimode beam (90), and any alternative or equivalent optical configurations may be also be used. Once combined, the combined multimode beam (92) passes through beam shaping optics (32) like those previously described. The resulting manipulated beam (92) may have improved power and uniform intensity characteristics suitable for sorting and analyzing particles at an interrogation zone.

EXAMPLE 1

A 150 mW UV diode laser having an initial beam width of about 6800 μm and beam height of about 1900 μm was operated at a wavelength in the range 370-380 nm was modified with beam shaping optics to produce a suitable sperm sorting configurations. The intensity of the beam profile can be seen in FIG. 4A. The laser was mounted at an appropriate orientation to provide a beam with suitable aspect ratio to match desired aspect ratio and beam profile at inspection point of flow cytometer.

The laser has a multi-mode transverse beam profile (M squared of greater than 1.5) and is shaped and or focused using optical elements (such as lenses/refractive elements, mirrors/reflective elements, phase elements, and the like) to alter the beam profile to provide sufficient intensity and uniformity for cell illumination at the inspection point. Specifically, a cylindrical lens with an 80 mm focal length was placed in the beam axis in order to compress the beam height in the flow axis. A second cylindrical lens with a focal length of 30 mm was placed in the beam axis, orthogonally to the first, to provide compression of the beam width in the transverse flow axis. This approach produced the pseudo Gaussian profile beam seen in FIG. 4B, by compressing the spatial modes of the laser beam a final beam spot was produced with a beam height about 24 μm in the flow axis and a beam width about 140 μm in the transverse flow axis.

Sperm nuclei stained with Hoechst 33342 was flowed though this beam spot in a sperm sorting configuration to produce two distinct populations (Seen as a histogram and bivariate plot in FIG. 5). By passing cells (to be measured) through the altered laser beam, scatter and or fluorescence light can be collected and with suitable spectral selection elements, be partitioned/separated to one or more detectors and measurements can be made to identify and characterize different cells such as in the case for sperm cells, the presence of an X or Y chromosome. This information can in turn be used to determine further processing steps on that cell such as selection, sorting, altering function of the cell as non-limiting examples.

EXAMPLE 2

A 200 mW UV diode laser having an initial beam width of 1700 μm and beam height of about 200 μm was operated at a wavelength in the range 370-380 nm was modified with beam shaping optics to produce a suitable sperm sorting configurations. The laser was mounted at an appropriate orientation to provide a beam with suitable aspect ratio to match desired aspect ratio and beam profile at inspection point of flow cytometer. Namely, the laser was mounted at 90 degrees (about beam axis) to provide an initial laser beam aspect ratio that is well suited to further beam shaping and focusing optics that provide sufficiently uniform cell illumination conditions. Specifically, the final desired aspect ratio was in the neighborhood of approximately 20 µm×160 µm.

The laser has a multi-mode transverse beam profile (M squared of greater than 1.5) and is shaped and or focused using optical elements (such as lenses/refractive elements, mirrors/reflective elements, phase elements, and the like) to alter the beam profile to provide sufficient intensity and uniformity for cell illumination at the inspection point. Specifically, a cylindrical lens with a 15 mm focal length was placed in the beam axis in order to compress the beam height in the flow axis. A second cylindrical lens with a focal length of 25 mm was placed in the beam axis, orthogonally to the first, to provide compression of the beam width in the transverse flow. This configuration produced a pseudo Gaussian profile beam, or other uniform beam profile by compressing the spatial modes of the laser beam. This arrangement of a crossed cylindrical lens pair are used to produce a 26 µm (vertical, cell flow axis) by 160 µm (horizontal, across flow axis) spot suitable for sorting sperm. These dimensions can be altered, for example to provide a 26 by 100 µm spot.

As can be easily understood from the foregoing, the basic concepts of the present invention may be embodied in a variety of ways. As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorter." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity; for example, "a container" refers to one or more of the containers. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. An instrument comprising:
    a flow source for delivering sperm along a flow axis to an interrogation zone;

a laser that produces a multimode beam along a beam axis which illuminates sperm at the interrogation zone, wherein the multimode beam has a transverse beam profile with multiple spatially separated intensity peaks;

beam shaping optics located on the beam axis which compress a beam height and a beam width of the transverse beam profile differently and focus the transverse beam profile to form a manipulated transverse beam profile with a pseudo-Gaussian intensity distribution at the interrogation zone, wherein the beam shaping optics highly compress the beam width, and wherein the manipulated transverse beam profile provides enough uniform laser exposure to sperm at the interrogation zone for sex sorting sperm;

a detector for detecting reflected and/or fluoresced light from the illuminated sperm at the interrogation zone and for producing a signal representative of particle characteristics; and a processor in communication with the detector for analyzing the signal and determining particle characteristics.

2. The instrument of claim 1 wherein the beam shaping optics further comprise:
a first element for altering the beam width of the transverse beam profile; and
a second element for altering the beam height of the transverse beam profile.

3. The instrument of claim 2 wherein the first element is located on the beam axis and comprises a cylindrical lens.

4. The instrument of claim 2 wherein the second element is located on the beam axis and comprises a cylindrical lens.

5. The instrument of claim 1 wherein the laser produces a multimode beam at a wavelength between 350 nm and 400 nm.

6. The instrument of claim 5 wherein the laser produces a multimode beam at a wavelength between 370 nm and 380 nm.

7. The instrument of claim 6 wherein the beam shaping optics comprises a pair of crossed cylindrical lenses.

8. The instrument of claim 7 wherein each crossed cylindrical lens is oriented 90 relative to the other lens.

9. The instrument of claim 8 wherein the first cylindrical lens has a focal length between 10 mm and 150 mm.

10. The instrument of claim 8 wherein the second cylindrical lens has a focal length of between 10 mm and 150 mm.

11. The instrument of claim 6 wherein the transverse beam profile is focused into a beam spot 26 μm by 160 μm.

12. The instrument of claim 6 wherein the transverse beam profile is focused into a beam spot 29 μm by 100 μm.

13. The instrument of claim 6 wherein the laser is oriented 90 degrees about the beam axis.

14. The instrument of claim 6 further comprising an orientating device for orienting sperm within the flow path.

15. The instrument of claim 6 further comprising a sorting device for sorting the sperm based upon the determined particle characteristics.

16. The instrument of claim 15 wherein the sorting devices comprises one selected from the group consisting of: deflection plates, a fluid switching element, and an ablation laser.

17. The instrument of claim 6 wherein the detector comprises a pair of orthogonal photo detectors.

18. The instrument of claim 6 wherein the laser comprises a UV multimode diode laser operated at 200 mW.

19. The instrument of claim 6 wherein the beam shaping optics comprises micro-electro-mechanical elements to redirect all, or portions of, the transverse beam profile to shape the transverse beam profile.

20. The instrument of claim 6 further comprising a second laser for producing a second multimode beam.

21. The instrument of claim 20 further comprises beam combining optics for producing a combined beam along the beam axis from the first and the second lasers, wherein the combined beam comprises higher power and more uniform intensity characteristics across the combined transverse beam profile as compared to either the first laser or the second laser alone.

22. A method of processing particles comprising:
flowing sperm along a fluid flow path having an interrogation zone;
producing a multimode beam directed at the interrogation zone, wherein the multimode beam has a transverse beam profile including multiple spatially separated intensity peaks;
compressing a beam height and a beam width of the transverse beam profile differently and focusing the transverse beam profile to create a manipulated transverse beam profile with pseudo-Gaussian intensity distribution at the interrogation zone, wherein the beam shaping optics highly compress the beam width, and wherein the manipulated transverse beam profile provides enough uniform laser exposure to sperm at the interrogation zone for sex sorting sperm;
illuminating sperm at the interrogation zone with the manipulated beam;
detecting reflected and/or fluoresced light from sperm as they pass the interrogation zone and producing a signal; and
classifying sperm based upon the produced signals.

23. The method of processing sperm according to claim 22 further comprising:
selecting sperm based on their classification; and
collecting selected sperm.

24. The method of processing sperm according to claim 22 wherein the step of compressing the transverse beam profile further comprises:
focusing the multimode beam; and
shaping the transverse beam profile.

25. The method of processing sperm according to claim 22 wherein the step of compressing the transverse beam profile further comprises:
compressing the beam height of the transverse beam profile with a first element to a beam height between 10 and 30 micrometers.

26. The method of processing sperm according to claim 25 wherein the step of compressing the transverse beam profile further comprises:
compressing the beam width of the beam profile to a beam width between 100 micrometers and 200 micrometers.

27. The method of processing sperm according to claim 22 further comprising: modifying the height to width ratio of the beam profile to between 1 to 4 and 1 to 5.

28. The method of processing sperm according to claim 22 wherein the step of compressing the transverse beam profile further comprises: focusing the multimode beam and varying the aspect ratio of the beam height to the beam width until the multiple spatially separated intensity peaks in the transverse beam profile are reduced or eliminated.

* * * * *

UNITED STATES PATENT AND TRADEMARK OFFICE
CERTIFICATE OF CORRECTION

Page 1 of 2

PATENT NO. : 9,442,059 B2
APPLICATION NO. : 14/114150
DATED : September 13, 2016
INVENTOR(S) : Johnathan Charles Sharpe et al.

It is certified that error appears in the above-identified patent and that said Letters Patent is hereby corrected as shown below:

In the Claims.

Column 9, Lines 39, 41, 48, 50, 54, 56, 59, 63 and 65, Claims 7, 8, 11-15, 17 and 18 should read.

7. The instrument of claim 1 wherein the beam shaping optics comprises a pair of crossed cylindrical lenses.

8. The instrument of claim 9 wherein each crossed cylindrical lens is oriented 90° relative to the other lens.

11. The instrument of claim 1 wherein the transverse beam profile is focused into a beam spot 26μm by 160μm.

12. The instrument of claim 1 wherein the transverse beam profile is focused into a beam spot 29μm by 100μm.

13. The instrument of claim 1 wherein the laser is oriented 90 degrees about the beam axis.

14. The instrument of claim 1 further comprising an orientating device for orienting sperm within the flow path.

15. The instrument of claim 1 further comprising a sorting device for sorting the sperm based upon the determined particle characteristics.

17. The instrument of claim 1 wherein the detector comprises a pair of orthogonal photo detectors.

18. The instrument of claim 1 wherein the laser comprises a UV multimode diode laser operated at 200mW.

Signed and Sealed this
Eighth Day of November, 2016

Michelle K. Lee
*Director of the United States Patent and Trademark Office*

CERTIFICATE OF CORRECTION (continued)
U.S. Pat. No. 9,442,059 B2

Column 10, Lines 1 and 5, Claims 19 and 20 should read.

19. The instrument of claim 1 wherein the beam shaping optics comprises micro-electro-mechanical elements to redirect all, or portions of, the transverse beam profile to shape the transverse beam profile.

20. The instrument of claim 1 further comprising a second laser for producing a second multimode beam.